United States Patent [19]

Grollier et al.

[11] Patent Number: 5,061,479
[45] Date of Patent: Oct. 29, 1991

[54] USE OF DIORGANOPOLYSILOXANES CONTAINING A 3-BENZYLIDENE CAMPHOR FUNCTIONAL GROUP IN COSMETICS AND NEW COSMETIC COMPOSITIONS CONTAINING THESE COMPOUNDS, INTENDED FOR PROTECTING THE SKIN AND HAIR

[75] Inventors: Jean F. Grollier; Herve Richard, both of Paris; Serge Forestier, Claye-Souilly; Gerard Lang, Saint Gratien, all of France

[73] Assignee: L'Oreal, Paris, France

[21] Appl. No.: 328,947

[22] Filed: Mar. 27, 1989

[30] Foreign Application Priority Data

Mar. 28, 1988 [LU] Luxembourg .......................... 87180

[51] Int. Cl.$^5$ .................. A61K 7/021; A61K 7/06; A61K 7/42; A61K 7/44; A61K 7/48; A61K 9/10; A61K 9/12
[52] U.S. Cl. ...................................... 424/47; 8/405; 8/406; 424/DIG. 1; 424/DIG. 2; 424/DIG. 5; 424/59; 424/60; 424/61; 424/62; 424/63; 424/64; 424/70; 424/071; 424/072; 424/073; 514/844; 514/845; 514/846; 514/847; 514/873; 514/880; 514/881; 514/937; 514/938; 514/944
[58] Field of Search ................. 424/47, 59, 70

[56] References Cited

U.S. PATENT DOCUMENTS

| | | | |
|---|---|---|---|
| 2,714,115 | 7/1955 | Holdstock | 424/59 X |
| 2,833,802 | 5/1958 | Merker | 424/59 |

FOREIGN PATENT DOCUMENTS

| | | | |
|---|---|---|---|
| 0138590 | 10/1984 | European Pat. Off. | 424/59 |
| 2188320 | 9/1987 | United Kingdom | 424/60 |

OTHER PUBLICATIONS

Seifen, Ole, Fette, Wachse, vol. 114, No. 2, 4 Fevrier 1988, pp. 51–54, Augsburg, DE; J. Roidl: "Bedeutung der Silicone in der modernen Kosmetik".
Kosmetika Aerosole Riechstoffe, Bedeutung der Silicone in der modernen Kosmetik by Josef Riodl, Seifen-Ole-Fette-Wachse-114, Jg. -Nr.2/1988, pp. 51-54.

*Primary Examiner*—Dale R. Ore
*Attorney, Agent, or Firm*—Marshall, O'Toole, Gerstein, Murray & Bicknell

[57] ABSTRACT

Use in cosmetics, as UV filters, of diorganopolysiloxanes containing a 3-benzylidenecamphor functional group of formula:

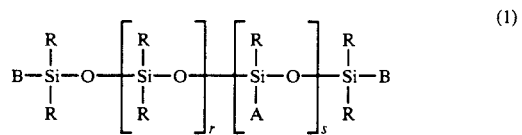

R being $C_1$–$C_{10}$ alkyl, phenyl or 3,3,3-trifluoropropyl, B denoting R or A, r=0–200, s=0–50, if s=0, at least one of the symbols B denotes A, or of formula:

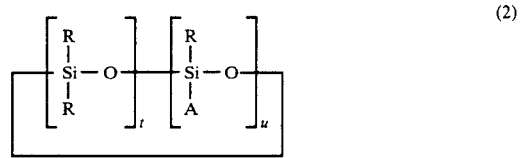

where
u=1–20 and t=0–20,
A and/or B denoting an optionally substituted alkylene or alkyleneoxy-3-benzylidenecamphor group.

17 Claims, No Drawings

USE OF DIORGANOPOLYSILOXANES CONTAINING A 3-BENZYLIDENE CAMPHOR FUNCTIONAL GROUP IN COSMETICS AND NEW COSMETIC COMPOSITIONS CONTAINING THESE COMPOUNDS, INTENDED FOR PROTECTING THE SKIN AND HAIR

The present invention relates to the use of diorganopolysiloxanes containing a 3-benzylidenecamphor functional group in cosmetics, particularly as agents filtering UV radiation, and to new cosmetic compositions containing these compounds, intended for protecting the skin and hair.

It is known that luminous radiations of wavelengths between 280 nm and 400 nm allow the human epidermis to tan and that rays of wavelengths between 280 and 320 nm, known by the name of UV-B, produce erythemas and skin burns, which may impair the development of the suntan; this UV-B radiation must therefore be filtered out.

It is also known that UV-A rays of wavelengths between 320 and 400 nm, which cause the skin to tan, are capable of inducing deterioration in the latter, particularly in the case of a sensitive skin or of a skin continually exposed to solar radiation. In particular, UV-A rays produce a loss of elasticity of the skin and the appearance of wrinkles, leading to premature aging. They promote the triggering of the erythematous reaction or amplify this reaction in some individuals and may even be at the source of phototoxic or photoallergic reactions.

It is therefore advantageous to have available compounds which absorb UV rays over a wide range, so as to be able to filter out both the UV-A and UV-B rays.

It is known, furthermore, that the constituents forming part of cosmetic preparations do not always have sufficient stability towards light and that they deteriorate under the effect of luminous radiations.

Consequently, it is desirable to incorporate in these preparations compounds which are capable of filtering out the UV rays and which must also exhibit good stability and sufficient solubility in the media usually employed in cosmetics, and in particular in oils and fats.

It is also desirable to ensure that hair is well protected against photochemical deterioration, particularly in order to avoid bleaching or a change in shade.

It is known, furthermore, to graft residues of molecules having a filtering effect towards UV radiation onto chains of synthetic carbonaceous polymers, of natural polymers, of protein hydrolysates or of polyamino amides; these graft polymers, described, for example, in French Patents Nos. 2,197,023, 2,237,912, 2,531,960, 2,548,018, 2,549,069, 2,586,692 and 2,586,693, may be employed to prepare cosmetic compositions which protect the human skin or which protect against sunlight. It has been found, however, that these graft polymers are generally poorly soluble in the usual cosmetic solvents, particularly in fatty substrates, and that they form films whose structure is too rigid.

Now, the Applicants have found that certain diorganopolysiloxanes containing a 3-benzylidenecamphor functional group exhibited, surprisingly, good cosmetic properties combined with good screening properties over a wide range of wavelengths stretching from 280 to 360 nm. In particular, they exhibit an excellent liposoluble nature, which means that they can be employed in the fatty substrates employed in cosmetics. In addition to their good screening capacity and their good solubility in fatty substances and the usual cosmetic solvents, these diorganopolysiloxanes containing a 3-benzylidenecamphor functional group exhibit an excellent chemical and photochemical stability and have the advantage of imparting softness to the skin and to hair, by which they are well tolerated.

The subject matter of the present invention is therefore the use in cosmetics, particularly as agents filtering out UV radiation of wavelengths between 280 and 360 nm, of diorganopolysiloxanes containing a 3-benzylidenecamphor functional group, chosen from those of formula:

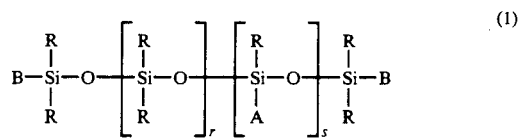

in which the symbols:
R, which are identical or different, are chosen from $C_1$-$C_{10}$ alkyl, phenyl and 3,3,3-trifluoropropyl radicals, at least 80% of the number of the radicals R being methyl radicals,
B, which are identical or different, are chosen from the R radicals and the radical A,
r is an integer chosen between 0 and 200 inclusive,
s is an integer chosen between 0 and 50 inclusive and if s is 0, at least one of the two symbols B denotes A,
and those of formula:

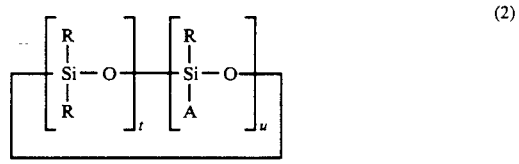

in which
R has the same meaning as in formula (1),
u is an integer between 1 and 20 inclusive, and
t is an integer between 0 and 20 inclusive,
t+u is equal to or greater than 3,
in which formulae the symbol A is a radical of formula:

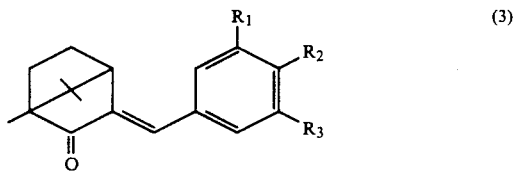

in which:
$R_1$ and $R_2$ denote a hydrogen atom, a $C_1$-$C_6$ alkyl radical, a $C_1$-$C_6$ alkoxy, hydroxyl or trimethylsilyloxy radical, or a divalent radical Y of formula:

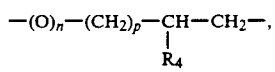

one of the two radicals $R_1$ and $R_2$ necessarily denoting the divalent radical Y,
$R_4$ denotes a hydrogen atom or a $C_1$-$C_4$ alkyl radical, n is 0 or 1,
p is an integer from 1 to 10 inclusive,
$R_3$ denotes a hydrogen atom, a $C_1$-$C_6$ alkyl radical or a $C_1$-$C_6$ alkoxy radical.

More particularly, random or block polymers of formula (1) or (2) exhibiting at least one of the following characteristics are employed:
R is methyl,
B is methyl,
r is between 5 and 20 inclusive,
s is between 2 and 15 inclusive,
t+u is between 3 and 10 inclusive,
$R_1$ is H or methoxy,
$R_2$ is H or methoxy,
one of the two radicals $R_1$ or $R_2$ denoting the divalent radical Y in which n=0 or 1, p=1, $R_4$=H or methyl,
$R_3$ is H or methoxy.

The polymers of formula (1) and (2) can be prepared from polymers in which all the radicals A are hydrogen atoms, called polymers containing SiH, of formulae (4) and (5):

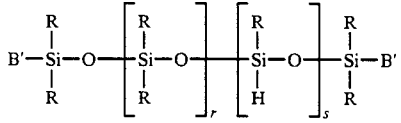

(4)

where R, r and s have the meaning given in the case of formula (1) and the radicals B', which are identical or different, are chosen from the radicals R and a hydrogen atom,

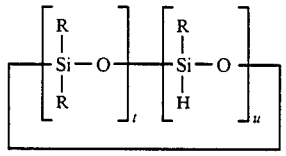

(5)

where R, t and u have the meaning given in formula (2).

Using these polymers containing SiH of formulae (4) or (5), a hydrosilylation reaction is carried out in the presence of a catalytically effective quantity of a platinum catalyst on an organic 3-benzylidenecamphor derivative of formula:

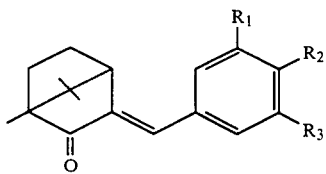

(6)

in which $R_1$, $R_2$ and $R_3$ have the same meaning as in formula (3), except that the radical Y is then the monovalent unsaturated homologous radical Y' of formula:

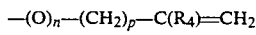

—(O)$_n$—(CH$_2$)$_p$—C(R$_4$)=CH$_2$ in which n, p and $R_4$ have the same meaning as in formula (3).

The compounds of formula (6) in which $R_2$ denotes the group —O(CH$_2$)$_p$—C(R$_4$)=CH$_2$ can be prepared as shown in French Patent No. 2,430,938, by reaction of the corresponding alkenyl halide with the corresponding p-hydroxy-3-benzylidenecamphor in the presence of sodium carbonate in dimethylformamide. The compounds of formula (6) in which $R_1$ denotes the group —(O)$_n$—(CH$_2$)$_p$—C(R$_4$)=CH$_2$ or $R_2$ the group —(CH$_2$)$_p$—C(R$_4$)=CH$_2$ can be prepared according to one of the following procedures:

1ST PROCEDURE

Preparation of the compounds of formula (6) in which $R_1$ denotes a radical —(O)$_n$—(CH$_2$)$_p$—C(R$_4$)=CH$_2$ or else $R_2$ denotes a radical —(CH$_2$)$_p$—C(R$_4$)=CH$_2$, where $R_1$, $R_2$, n, p, $R_4$ and $R_3$ have the meanings shown above.

An aromatic aldehyde of formula (II) is condensed with synthetic camphor (d,l-camphor) or natural camphor (d-camphor) according to the following reaction scheme:

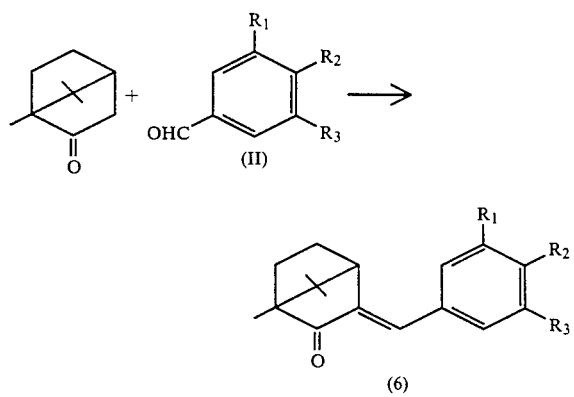

This reaction is carried out in the presence of a base, for example in the presence of an alkali metal amide, hydride or alcoholate, in an inert solvent such as benzene, toluene, ether, dioxane or 1,2-dimethoxyethane, at a temperature of between 0° C. and the boiling point of the solvent.

a) The aldehyde of formula (II) in which $R_1$ denotes a radical —(O)$_n$—(CH$_2$)$_p$—C(R$_4$)=CH$_2$ when n=1, may be obtained by reaction of an alkenyl halide of formula (III) with an aldehyde of formula (IIA) according to the following reaction scheme:

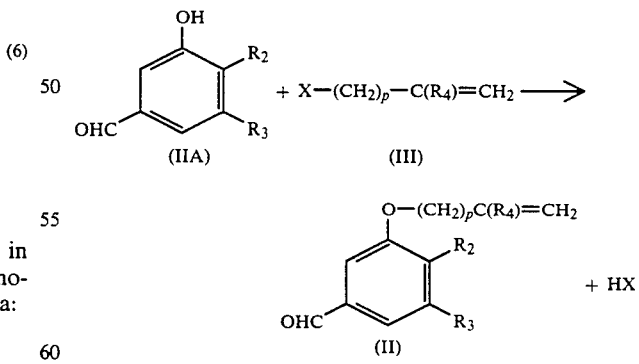

This reaction is carried out in the presence of a base in a solvent, for example in the presence of an alkali metal or alkaline-earth metal carbonate or hydroxide or of an alkali metal amide, hydride or alcoholate, in a solvent compatible with the nature of the base, such as water or an organic solvent such as dimethylformamide, dimethyl sulphoxide, dioxane or an alcohol, at a temperature between the ambient temperature and the boiling point of the solvent.

In the aldehyde of formula (IIA), which may be prepared according to known methods, and in the aldehyde of formula (II) in which $R_1$ denotes a radical —(O—)—$(CH_2)_p$—$C(R_4)=CH_2$, $R_2$ and $R_3$ denotes a hydrogen atom, a $C_1$–$C_6$ alkyl radical or a $C_1$–$C_6$ alkoxy radical. In the compound of formula (III), X denotes a halogen atom, preferably chlorine or bromine, and $R_4$ and p have the meanings referred to above.

b) The aldehyde of formula (II) in which $R_1$ denotes a radical —$(O)_n$—$(CH_2)_p$—$C(R_4)=CH_2$ when n=0, or in which $R_2$ denotes a radical —$(CH_2)_p$—$C(R_4)=CH_2$, may be obtained by reaction of ethyl orthoformate with a phenylmagnesium bromide of formula (IV), followed by a hydrolysis of the acetal formed, according to the following reaction scheme:

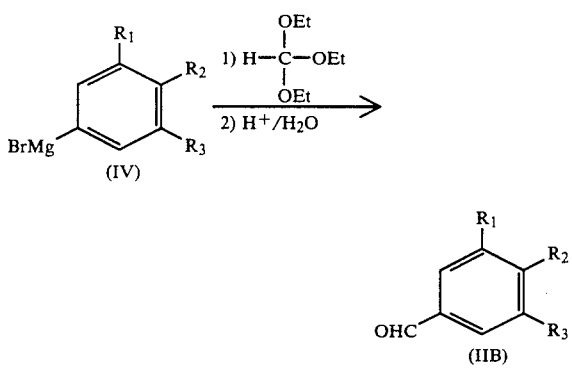

This reaction may be carried out under the conditions described by Quelet (C. R. Acad. Science vol. 182, p. 1285 and Bull. Soc. Chim. Fr. vol. 45, p. 267), for example in an inert solvent such as ethyl ether, dioxane or 1,2-dimethoxyethane, at a temperature between the ambient temperature and the boiling point of the solvent.

In the compounds of formula (IIB) and (IV), one of the substituents $R_1$ or $R_2$ denotes a radical $(CH_2)_p$—$C(R_4)=CH_2$, $R_4$ and p having the meaning referred to above, and the other denotes a hydrogen atom, a $C_1$–$C_6$ alkyl radical or a $C_1$–$C_6$ alkoxy radical, and $R_3$ denotes a hydrogen atom, a $C_1$–$C_6$ alkyl radical or a $C_1$–$C_6$ alkoxy radical.

2ND PROCEDURE

Preparation of the compounds of formula (6) in which $R_1$ denotes a radical —$(O)_n$—$(CH_2)_p$—$C(R_4)=CH_2$ when n is equal to 1 (compounds IA).

These compounds can be obtained by reaction of an alkenyl halide of formula (III) with a 3'-hydroxy-3-benzylidenecamphor of formula (V) in the presence of a base, for example in the presence of an alkali metal or alkaline-earth metal hydroxide or carbonate or of an alkali metal amide, alcoholate or hydride, in a solvent compatible with the nature of the base, such as water or an organic solvent such as an alcohol, dioxane, dimethylsulphoxide or dimethylformamide, at a temperature between the ambient temperature and the boiling point of the solvent, according to the following reaction scheme:

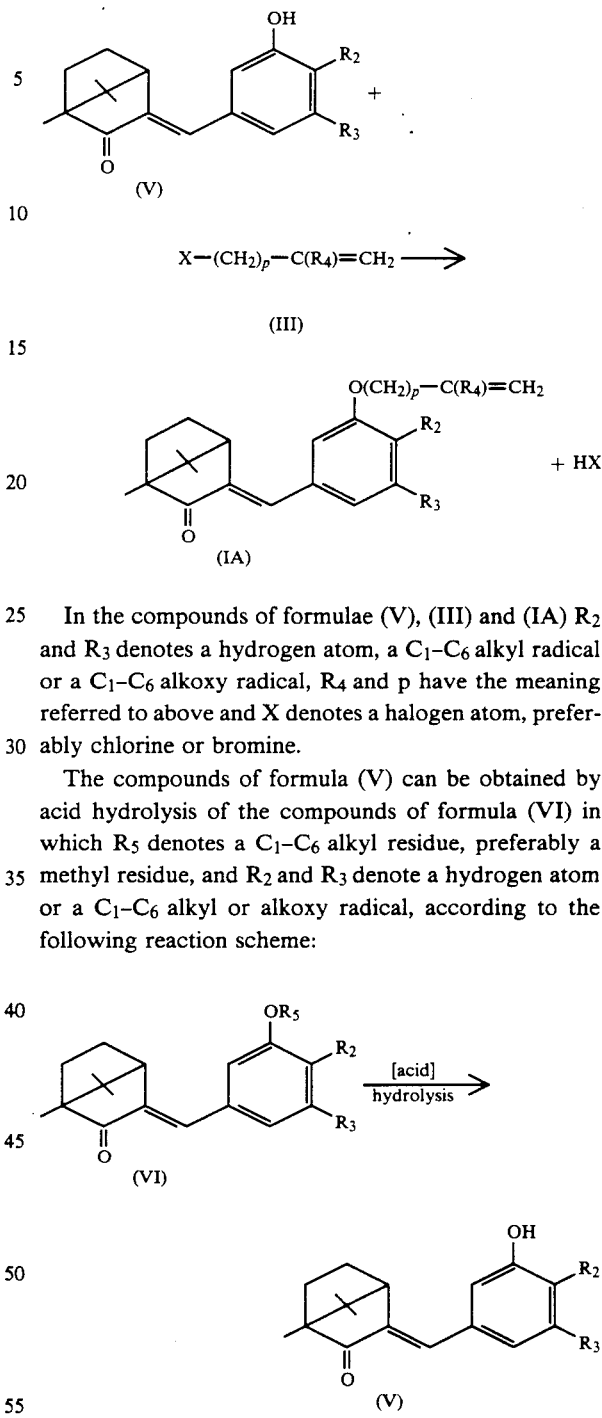

In the compounds of formulae (V), (III) and (IA) $R_2$ and $R_3$ denotes a hydrogen atom, a $C_1$–$C_6$ alkyl radical or a $C_1$–$C_6$ alkoxy radical, $R_4$ and p have the meaning referred to above and X denotes a halogen atom, preferably chlorine or bromine.

The compounds of formula (V) can be obtained by acid hydrolysis of the compounds of formula (VI) in which $R_5$ denotes a $C_1$–$C_6$ alkyl residue, preferably a methyl residue, and $R_2$ and $R_3$ denote a hydrogen atom or a $C_1$–$C_6$ alkyl or alkoxy radical, according to the following reaction scheme:

This hydrolysi may be carried out in the presence of a hydrolysing agent such as, for example, pyridine hydrochloride, at a temperature close to the boiling point of the reaction mixture.

The compounds of formula (V) can also be prepared by condensation of an aldehyde of formula (IIA) with by condensation of an aldehyde of formula (IIA) with synthetic camphor (d,l-camphor) or natural camphor (d-camphor), according to the following reaction scheme:

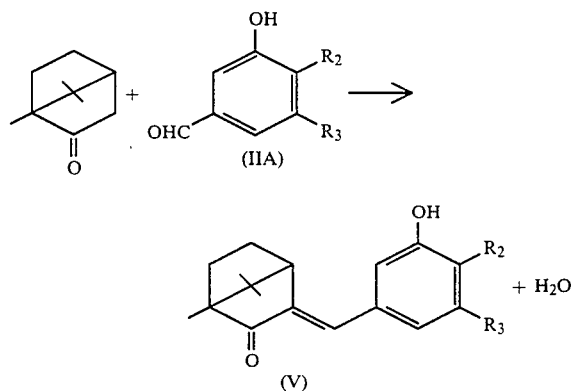

$R_2$ and $R_3$ denoting a hydrogen atom or a $C_1$–$C_6$ alkyl or alkoxy radical.

This reaction is carried out in the presence of a base in a solvent, for example by means of sodium hydride or potassium tert-butylate in dioxane or 1,2-dimethoxyethane, at a temperature between the ambient temperature and the boiling point of the solvent.

3RD PROCEDURE

Preparation of the compounds of formula (6) in which $R_1$ denotes a radical —$(O)_n$—$(CH_2)_p$—$C(R_4)$=$CH_2$ when $n=0$ and $p=1$ (compounds ID).

These compounds can be obtained by a Claisen rearrangement of a compound of formula (IB) according to the reaction scheme below:

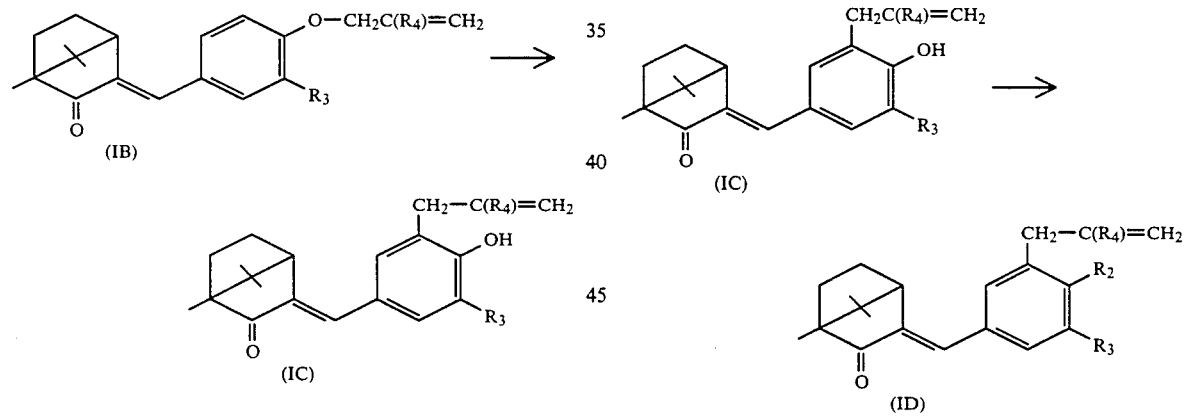

In the compounds (IB) and (IC) $R_3$ and $R_4$ have the meanings referred to above.

The compound (IB) can be prepared in a known manner, by reacting a 4'-hydroxy-3-benzylidenecamphor of formula (VII) with an alkenyl halide of formula (III) in which $p=1$, according to the scheme:

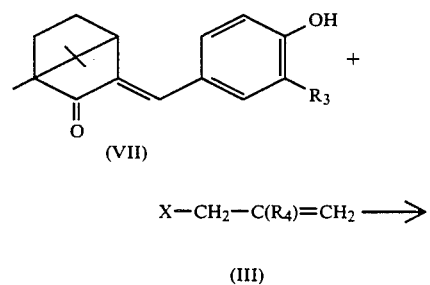

$R_3$ and $R_4$ having the meanings referred to above and X being a halogen, preferably chlorine or bromine. This reaction takes place in the presence of a base, for example an alkali metal or alkaline-earth metal carbonate or hydroxide, or an alkali metal amide, alcoholate or hydride, in a solvent compatible with the nature of the base, such as water or an organic solvent, for example an alcohol, dioxane, dimethyl sulphoxide or dimethylformamide, at a temperature between the ambient temperature and the boiling point of the solvent.

The Claisen rearrangement may be carried out under the conditions described by Tarbell (Organic Reactions, vol. 2, John Wiley, New York, 1944, page 1), by heating the compound of formula (IB) to at least approximately 170° C., optionally in the presence of a solvent.

The compound of formula (IC) thus obtained is converted into a compound of formula (ID) in which $R_2$ denotes a $C_1$–$C_6$ alkoxy radical by reaction with a $C_1$–$C_6$ alkyl halide in the presence of a base, for example an alkali metal carbonate, in a solvent such as dimethylformamide, or else in the presence of an alkali metal hydride in 1,2-dimethoxyethane, according to the following reaction scheme:

In the compound (ID), $R_2$ denotes a $C_1$–$C_6$ alkoxy radical and $R_3$ and $R_4$ have the meaning referred to above.

The platinum catalysts applied in carrying out the hydrosilylation reaction of the polymers of formulae (4) or (5) with the organic derivative of formula (6) are amply described in the literature. There may be mentioned, in particular, the complexes of platinum and of an organic product described in U.S. Patents U.S. Pat. No. 3,159,601, U.S. Pat. No. 3,159,602, U.S. Pat. No. 3,220,972 and European Patents EP-A-57,459, EP-A-188,978 and EP-A-190,530 and the complexes of platinum and of a vinylated organopolysiloxane, which are described in U.S. Patents, U.S. Pat. No. 3,419,593, U.S. Pat. No. 3,715,334, U.S. Pat. No. 3,377,432 and U.S. Pat. No. 3,814,730.

To react the polymer containing SiH of formula (4) or (5) with the derivative of formula (6), a quantity of platinum catalyst is generally employed which, calculated as the weight of platinum metal, is between 5 and 600 ppm, preferably between 10 and 200 ppm, based on the weight of polymer containing SiH of formula (4) or (5).

The hydrosilylation reaction can take place in bulk or in a volatile organic solvent such as toluene, heptane, xylene, tetrahydrofuran and tetrachloroethylene.

It is generally desirable to heat the reaction mixture to a temperature of 60° to 120° C. for the time needed for the reaction to be complete. Furthermore, it is desirable to add the polymer containing SiH drop by drop to the derivative of formula (6) in solution in an organic solvent.

A check that the reaction is complete is performed by determining the residual SiH groups with alcoholic potassium hydroxide, and the solvent is then removed, for example by distillation under reduced pressure.

The crude oil obtained may be purified, for example by being passed through a silica absorbent column.

Another subject of the invention consists of the cosmetic compositions intended to protect the skin and hair from UV radiation, containing an effective quantity of a diorganopolysiloxane containing a 3-benzylidenecamphor functional group of formula (1) or (2), in a cosmetically acceptable medium.

Another subject of the invention is a process for protecting the skin and hair, natural or sensitized towards solar radiation, consisting in applying to the skin or hair an effective quantity of at least one compound of formula (1) or (2) contained in a cosmetically acceptable substrate comprising at least one fatty phase.

"Sensitized hair" means hair which has undergone a permanent-waving, dyeing or bleaching treatment.

A further subject of the invention is a coloured or uncoloured cosmetic composition, stabilized against light, comprising an effective quantity of at least one diorganopolysiloxane containing a 3-benzylidenecamphor functional group of formula (1) or (2) above.

When it is employed as a composition intended to protect the human epidermis against the ultraviolet rays, the cosmetic composition according to the invention may take the most diverse forms usually employed for a composition of this type. In particular, it may take the form of oily, alcoholic or oleoalcoholic lotions, of emulsions such as a cream or a milk, of oleoalcoholic, alcoholic or hydroalcoholic gels, of solid sticks, or it may be packaged as an aerosol.

It may contain cosmetic adjuvants which are usually employed in a composition of this type, such as thickeners, softeners, humectants, surfactants, preserving agents, antifoams, perfumes, oils, waxes, lanolin, propellants, dyes and/or pigments intended to colour the composition itself or the skin, or any other ingredient usually employed in cosmetics.

The compound of formula (1) or (2) is present in proportions by weight of between 0.25 and 3% relative to the total weight of the cosmetic composition protecting the human epidermis.

The solubilization solvent employed may be an oil, a wax and, in general, any fatty substance, a lower monoalcohol or polyol, a benzoate based on $C_{12}$-$C_{15}$ alcohols, or mixtures thereof. The monoalcohols or polyols which are more particularly preferred are ethanol, isopropanol, propylene glycol, glycerine and sorbitol.

An embodiment of the invention is an emulsion in the form of protective cream or milk comprising, in addition to the compound of formula (1) or (2), fatty alcohols, fatty acid esters and particularly fatty acid triglycerides, fatty acids, lanolin, natural or synthetic oils or waxes and emulsifers, in the presence of water.

Another embodiment consists of oily lotions based on natural or synthetic oils and waxes, lanolin, and fatty acid esters, especially fatty acid triglycerides, or of oleoalcoholic lotions based on a lower alcohol such as ethanol or a glycol such as propylene glycol and/or a polyol such as glycerine and oils, waxes and fatty acid esters such as fatty acid triglycerides.

The cosmetic composition of the invention may also be an alcoholic gel comprising one or more lower alcohols or polyols such as ethanol, propylene glycol or glycerine and a thickener such as silica. The oleoalcoholic gels additionally contain an oil or a natural or synthetic wax.

The solid sticks consist of natural or synthetic waxes and oils, fatty alcohols, fatty acid esters, lanolin and other fatty substances.

In the case of a composition packaged as an aerosol, conventional propellants are employed, such as alkanes, fluoroalkanes and chlorofluoroalkanes.

The present invention is also aimed at cosmetic compositions for protection against sunlight, containing at least one compound of formula (1) or (2) and capable of containing other UV-B and/or UV-A sunscreens.

In this case, the compound of formula (1) or (2) is present in concentrations which vary from 0.5 to 10% by weigth, and the total quantity of sunscreens present in the composition for protection against sunlight, that is to say the compound of formula (1) or (2) and optionally the other sunscreens, is between 0.5 and 15% by weight relative to the total weight of the composition for protection against sunlight.

These compositions for protection against sunlight are in the forms indicated above in the case of the compositions for protecting the human epidermis.

When the cosmetic composition according to the invention is intended to protect natural or sensitized hair against UV rays, this composition may take the form of a shampoo, lotion, gel or rinsing emulsion, to be applied before or after shampooing, before or after dyeing or bleaching, before or after permanent waving, of a styling or treating lotion or gel, of a lotion or gel for blow-drying or setting hair, a covering spray, hair lacquer, or a composition for permanent-waving, dyeing or bleaching hair. In addition to the compound of the invention, this composition may contain various adjuvants employed in a composition of this type, such as surface-active agents, thickeners, polymers, softeners, preserving agents, foam stabilizers, electrolytes, organic solvents, silicone derivatives, oils, waxes, antigrease agents, dyes and/or pigments intended to colour the composition itself or the hair or any other ingredient usually employed in the field of hair care.

It contains 0.25 to 5% by weight of compound of formula (1) or (2).

The present invention is also aimed at the cosmetic compositions including a light-sensitive constituent and containing at least one compound of formula (1) or (2) as a protective agent against ultraviolet rays. These cosmetic compositions consist of hair-care compositions such as hair lacquers, hair-setting lotions, optionally treating or disentangling, colouring shampoos, hair-dyeing compositions, of makeup products such as nail varnishes, creams and oils for treating the epidermis, foundations, lipsticks, compositions for skin care such as bath oils or creams, as well as any other cosmetic composition which, as a result of its constituents, may present problems of stability to light during storage.

Such compositions contain 0.25 to 3% by weight of compound of formula (1) or (2).

The invention is also aimed at a process for protecting cosmetic compositions against ultraviolet rays, consisting in incorporating an effective quantity of at least one compound of formula (1) or (2) in these compositions.

The examples below illustrate the invention without limiting its scope.

REFERENCE EXAMPLE 1

Into a three-necked round-bottom flask maintained at 96° C. by means of an oil bath, fitted with a central stirrer and a vertical condenser, are charged 110.8 g (0.374 mole) of 4'-allyloxy-3-benzylidenecamphor prepared in accordance with Example 8 of FR-A-2,430,938, 160 g of toluene and 12 μl of a hexane solution (containing 8.45% by weight of platinum metal) of a platinum complex prepared from hexachloroplatinic acid and 1,3-divinyl-1,1,3,3-tetramethyldisiloxane as described in Patent U.S. Pat. No. 3,814,730.

50 g of a random polymer containing SiH, of formula:

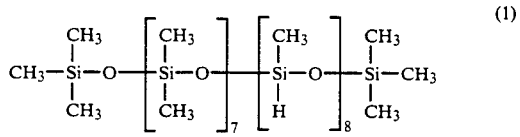

analysed by titration at 731.3 meq/100 g as SiH functional group (meq=milliequivalent), are added over half an hour.

After 10 hours' reaction a check is made, by determining the residual SiH groups using butanolic potassium hydroxide, that the degree of conversion of the SiH functional groups is 99%.

A clear, slightly yellow oil, of very high viscosity, is then obtained, after the toluene has been removed by distillation at 100° C. under a reduced pressure of 0.66 kPa.

A proton nuclear magnetic resonance analysis ($^1$H-NMR) is carried out on a sample of the oil obtained, at 360 MHz in CDCl$_3$. The NMR spectrum is consistent with the expected structure.

The proportion of the initial camphor derivative in the oil obtained after removal of the solvent is 6.4% by weight.

The removal of this derivative is easily performed by passing the oil through a column of silica gel (Kiselgel ART 7 754 support, marketed by Merck) with a 95/5 volume mixture of hexane/butyl acetate as an elution solvent for the organic derivative and with butyl acetate as an elution solvent for the oil.

The purified oil contains less than $3 \times 10^{-3}$% by weight of the initial camphor derivative. It has a refractive index of approximately 1.542 and the UV spectrum in chloroform gives the following results:

$\lambda_{max} = 316$ nm $E(1\%) = 576$,

E being the optical density measured at the wavelength of maximum absorption $\lambda_{max}$ for a solution containing 1% by weight of sunscreen product.

REFERENCE EXAMPLE 2

Preparation of 4'-allyloxy-3'-methoxy-3-benzylidenecamphor.

The operating procedure of Example 8 of French Patent FR-A-2,430,938 is repeated exactly, except that 4'-hydroxy-3'-methoxy-3-benzylidenecamphor is employed as starting material. The desired product, which has a melting point of 75° C., is obtained.

The same operations as in Example 1 are then carried out, except that the following are employed:
30.6 g of 4'-allyloxy-3'-methoxy-3-benzylidene camphor,
31 g of toluene,
3.4 μl of platinum catalyst solution, and
12.5 g of polymer containing SiH, of formula:

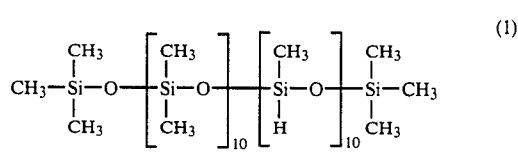

analysed by titration at 733.9 meq/100 g as SiH functional group (meq=milliequivalent).

A degree of conversion of the SiH groups of 99% is obtained after 9 hours' reaction.

After removal of the toluene, 40.0 g of a very viscous, slightly yellow oil are obtained, analysed by titration at 5.3% by weight of the initial camphor derivative.

The $^1$H-NMR analysis confirms the expected structure.

The removal of the camphor derivative is carried out in the same way as in Example 1, except that the elution solvent for the camphor derivative is dichloromethane.

The purified oil contains less than $3 \times 10^{-3}$% by weight of camphor derivative and has a refractive index of approximately 1.540.

The UV spectrum in chloroform gives the following results:

$\lambda_{max} = 327$ nm $E(1\%) = 416$

REFERENCE EXAMPLE 3

3a-Preparation of
3'-allyl-4'-methoxy-3-benzylidenecamphor

1st Stage

Preparation of
3'-allyl-4'-hydroxy-3-benzylidenecamphor 296 g (1 mole) of 4'-allyloxy-3-benzylidenecamphor obtained in accordance with Example 8 of FR-A-2,430,938 are heated for 24 hours with stirring to 185° C.

The cooled reaction mixture is recrystallized from ethyl ether. 270 g of 3'-allyl-4'-hydroxy-3-benzylidenecamphor which has the following characteristics are thus obtained:
melting point: 150° C.
$^1$H-NMR spectrum (CDCl$_3$): spectrum in accordance with the expected structure UV spectrum (ethanol) $\lambda_{max}$: 327 nm; $\epsilon$: 22600
elemental analysis calculated %: C, 81.04; H 8.16.
found %: C, 81.11; H 8.18.

2nd Stage

Preparation of
3'-allyl-4'-methoxy-3-benzylidenecamphor 9 g (0.03 mole) of 3'-allyl-4'-hydroxy-3-benzylidenecamphor obtained in the first stage above are dissolved in 150 cm³ of 1,2-dimethoxyethane, dried over molecular sieve beforehand. 2.56 g of sodium hydride are added slowly and the mixture is heated to 60° C. 8.52 g (0.06 mole) of methyl iodide are introduced dropwise, and the mixture is then heated under reflux for 2 hours. The solvent is evaporated off and the residue is taken up with 50 cm³ of ethyl ether. The ether phase is washed twice with water and is then dried over sodium sulphate. After evaporation of the solvent, 8.8 g of 3'-allyl-4'-methoxy-3-benzylidenecamphor are recovered in the form of white crystals which have the following characteristics:

melting point: 37° C.

¹H-NMR spectrum (CDCl₃): spectrum in accordance with the expected structure

UV spectrum (95° ethanol) $\lambda_{max}$: 322 nm; $\epsilon$: 23600.

Elemental analysis: Calculated %: C, 81.25; H 8.44 O 10.31. Found %: C, 81.35; H 8.60 O 10.50.

3b-Preparation of the polydimethylsiloxane of formula

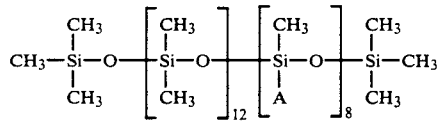

(1)

where A is the organic radical of formula:

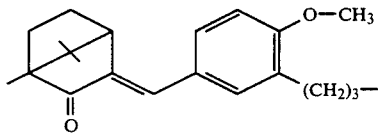

25 g (80.53 mmoles) of 3'-allyl-4'-methoxy-3-benzylidenecamphor and 25 g of toluene are charged into a three-necked round-bottom flask maintained at 100° C. by means of an oil bath, fitted with a central stirrer and a vertical condenser.

When the temperature of the reaction medium is 100° C., 1.60 microliters of a hexane solution (containing 9.92% by weight of platinum metal) of the platinum complex employed in Example 1 above are introduced.

10.37 g of a random polymer containing SiH, of formula:

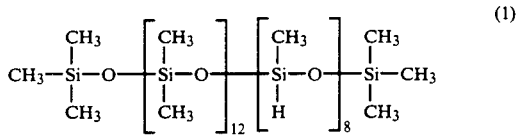

(1)

analysed by titration at 705.8 meq/100 g as SiH functional group, are then added over 1 hour 30 minutes.

The degree of conversion of the SiH groups is quantitative after 11 hours' reaction.

After removal of the toluene, a viscous yellow oil is isolated, analysed by titration at 11.7% by weight of the initial camphor derivative.

The ¹H-NMR analysis and the ²⁹Si-NMR analysis at 49.7 MHz in CDCl₃ + Fe(Acac)₃ show that the product is in accordance with the expected structure.

The removal of the initial camphor derivative is carried out in the same way as in Example 1.

The purified oil contains less than $3 \times 10^{-3}$% by weight of initial camphor derivative.

The UV spectrum in chloroform shows that:

$\lambda_{max} = 322$ nm

EXAMPLE 1

A sun cream of the following composition is prepared:

| | |
|---|---|
| Polydimethylsiloxane with 4'-allyloxy-3-benzylidene camphor grafts of reference Example 1 | 5 g |
| Mixture of cetylstearyl alcohol (80%) and cetylstearyl alcohol oxyethylenated with 33 moles of ethylene oxide (20%) sold by Henkel under the name "Sinnowax AO" | 7 g |
| Glycerol monostearate | 2 g |
| Cetyl alcohol | 1.5 g |
| Benzoate of C₁₂-C₁₅ alcohols sold by Witco under the name "Finsolv TN" | 15 g |
| Glycerine | 20 g |
| Polydimethylsiloxane | 1.5 g |
| Perfume, preserving agent q.s. | |
| Water q.s. | 100 g |

This cream is prepared according to conventional methods for preparing emulsions by dissolving the sunscreen in the fatty phase containing the emulsifiers, heating this fatty phase to about 70-80% and adding, with vigorous stirring, water heated to the same temperature; stirring is continued for 10 to 15 minutes and the product is then allowed to cool with moderate stirring and at about 40° C. the perfume and preserving agent are added.

EXAMPLE 2

A sun cream of the following composition is prepared in the same manner as in Example 1:

| | |
|---|---|
| Polydimethylsiloxane containing 4'-allyloxy-3-benzylidenecamphor grafts of reference Example 1 | 3.5 g |
| Liquid lanolin | 7 g |
| Triglyceride of C₁₀-C₁₈ fatty acids, sold under the name "Nesatol" by Vevy | 5 g |
| Ester of polyethoxylated oleic acid and of glycerol sold under the name "Labrafil M 1969 CS" by Gattefosse | 2.5 g |
| Mixture of glycerol stearate and of polyethylene glycol stearate containing 100 moles of ethylene oxide, sold under the name "Arlacel 165" by ICI | 5 g |
| Stearyl alcohol | 1 g |
| Stearic acid | 2.5 g |
| Benzoate of C₁₂-C₁₅ alcohols, sold under the name "Finsolv TN" by Witco | 9 g |
| Mixture of cetyl phosphate and of cetyl/diethanolamine phosphate sold under the name "Amphisol" by Givaudan | 0.5 g |
| Triethanolamine | 0.2 g |
| Preserving agent, perfume q.s. | |
| Water q.s. | 100 g |

EXAMPLE 3

An after-shampoo of the following composition is prepared:

| | |
|---|---|
| Polydimethylsiloxane containing 4'-allyloxy-3-benzylidenecamphor grafts of reference Example 1 | 2 g |
| Mixture of cetylstearyl alcohol (80%) and cetylstearyl alcohol oxyethylenated with 33 moles of ethylene oxide (20%) sold by Henkel under the name "Sinnowax AO" | 3 g |
| Cetyl alcohol | 1 g |
| Stearyl alcohol | 1 g |
| Triethanolamine q.s. pH: 7.3 | |
| Water q.s. | 100 g |

The cetyl and stearyl alcohols and the Sinnowax AO are melted at about 60°–70° C.; the polydimethylsiloxane containing 4'-allyloxy-3-benzylidenecamphor grafts is dissolved at this temperature. The mixture is allowed to return to ambient temperature and is then diluted with water; triethanolamine is added to adjust the pH to 7.3.

EXAMPLE 4

A hair protection spray of the following composition is prepared:

| | |
|---|---|
| Polydimethylsiloxane containing 4'-allyloxy-3-benzylidenecamphor grafts of reference Example 1 | 2 g |
| Benzoate of $C_{12}$–$C_{15}$ alcohols, sold by Witco under the name "Finsolv TN" | 12 g |
| Ethyl alcohol q.s. | 100 g |

The above composition is packaged in a pump bottle.

The polydimethylsiloxane containing 4'-allyloxy-3-benzylidenecamphor grafts is dissolved in Finsolv TN at ambient temperature; ethyl alcohol is added to make up 100 g.

EXAMPLE 5

A sun milk (O/W emulsion) of the following composition is prepared:

| | |
|---|---|
| Cetyl alcohol/stearyl alcohol (30/70) mixture | 2.4 g |
| Mixture of cetyl alcohol and stearyl alcohol oxyethylenated with 33 moles of ethylene oxide (30/70) | 0.6 g |
| Mixture of glycerol mono- and distearate, not autoemulsifiable | 1 g |
| Vaseline oil | 6 g |
| Isopropyl myristate | 3 g |
| Silicone DC 200-350, CST sold by Dow Corning | 1 g |
| Pure cetyl alcohol | 1 g |
| Pure stearyl alcohol | 2 g |
| Polydimethylsiloxane containing 4'-allyloxy-3'-methoxy-3-benzylidenecamphor grafts of reference Example 2 | 0.5 g |
| 2-Ethylhexyl p-methoxycinnamate | 2 g |
| Aqueous phase | |
| Glycerine | 20 g |
| Preserving agents q.s. | |
| Perfume q.s. | |
| Water q.s. | 100 g |

This milk is prepared by adding the fatty phase heated to 80° C. to the aqueous phase, heated to the same temperature, with stirring.

EXAMPLE 6

A protective gel for the skin and hair, of the following composition, is prepared:

| | |
|---|---|
| Polydimethylsiloxane containing 4'-allyloxy-3'-methoxy-3-benzylidenecamphor grafts of reference Example 2 | 0.5 g |
| Diethylene glycol monobutyl ether | 10 g |
| Crosslinked polyacrylic acid, MW = 4,000,000, sold by Goodrich under the name "Carbopol 940" | 1 g |
| Water q.s. | 100 g |
| Triethanolamine q.s. pH: 6.8 | |

EXAMPLE 7

A cream for skin care, of the following composition, is prepared:

| | |
|---|---|
| Polydimethylsiloxane containing 4'-allyloxy-3'-methoxy-3-benzylidenecamphor grafts of reference Example 2 | 1 g |
| Diethylene glycol monobutyl ether | 10 g |
| Mixture of cetylstearyl alcohol and of cetylstearyl alcohol oxyethylenated with 33 moles of ethylene oxide, sold under the name "Sinnowax AO" by Henkel | 2 g |
| Pure stearyl alcohol | 1 g |
| Pure cetyl alcohol | 1 g |
| Xanthan gum sold by Kelco under the name "Keltrol T" | 0.7 g |
| Water q.s. | 100 g |
| HCl q.s. pH: 5.8 | |

EXAMPLE 8

A protective gel for the skin and hair similar to that of Example 6 is prepared using 0.5 g of polydimethylsiloxane containing 3'-allyl-4'-methoxy-3-enzylidenecamphor of reference Example 3.

EXAMPLE 9

| Treatment lotion for hair | |
|---|---|
| Polydimethylsiloxane containing 4'-allyloxy-3-benzylidenecamphor grafts of reference Example 1 | 5 g |
| Benzoate of $C_{12}$–$C_{15}$ alcohols, sold under the name of "Finsolv TN" by Witco | 65 g |
| Isoparaffin sold under the name of "Isopar H" by Exxon Chemicals | 35 g |

This clear lotion promotes the disentangling of wet hair and of dry hair, while protecting it against ultraviolet radiation.

We claim:

1. A cosmetic composition for protecting the skin and hair against degradation due to ultraviolet radiation, comprising a cosmetically acceptable medium and an effective quantity of at least one diorganopolysiloxane having a 3-benzylidenecamphor functional group, said diorganopolysiloxane having either of the formulas:

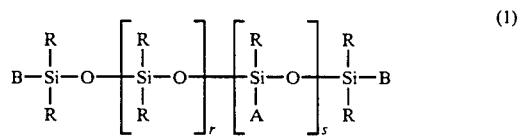

and

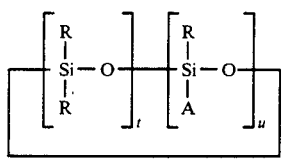 (2)

in which:
substituents R, which can be identical or different, are $C_1$–$C_{10}$ alkyl, phenyl or 3,3,3-trifluoropropyl, at least 80% of substituents R being methyl,
A is a radical of formula:

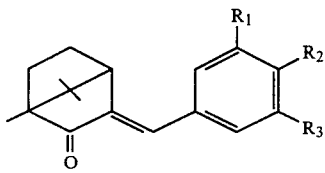 (3)

$R_1$ and $R_2$ independently represent hydrogen, $C_1$–$C_6$ alkyl, $C_1$–$C_6$ alkoxy, hydroxyl, trimethylsilyloxy or a divalent radical Y of formula:

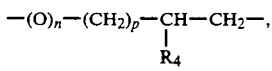

one of $R_1$ and $R_2$ necessarily representing Y,
$R_4$ is hydrogen or $C_1$–$C_4$ alkyl,
n is 0 or 1,
p is an integer from 1 to 10 inclusive,
$R_3$ is hydrogen, $C_1$–$C_6$ alkyl, or $C_1$–$C_6$ alkoxy,
substituents B, which can be identical or different, are R or A,
r is an integer from 0 to 200 inclusive,
s is an integer from 0 to 50 inclusive, provided that if s is 0, at least one of B is A,
t is an integer from 0 to 20 inclusive,
u is an integer from 1 to 20 inclusive, provided that t+u is equal to or greater than 3.

2. A cosmetic composition according to claim 1 wherein said diorganopolysiloxane has at least one of the following characteristics:
R is methyl, B is methyl, r is between 5 and 20 inclusive, s is between 2 and 15 inclusive, t+u is between 3 and 10 inclusive, $R_1$ is H or methoxy, $R_2$ is H or methoxy, one of $R_1$ and $R_2$ necessarily representing Y wherein n is 0 or 1, p is 1, $R_4$ is H or methyl, and $R_3$ is H or methoxy.

3. A cosmetic composition according to claim 1 comprising a polydimethylsiloxane having 4'-allyloxy-3-benzylidenecamphor grafts of formula (1) in which R and B are methyl, r is equal to 7 and s is equal to 8.

4. A cosmetic composition according to claim 1 comprising a polydimethylsiloxane having 4'-allyloxy-3'-methoxy-3-benzylidenecamphor grafts of formula (1) in which R and B are methyl, r is equal to 10 and s is equal to 10.

5. A cosmetic composition according to claim 1 comprising a polydimethylsiloxane having 3'-allyl-4'-methoxy-3-benzylidenecamphor grafts of formula (1) in which R and B are methyl, r is equal to 12 and s is equal to 8.

6. A cosmetic composition according to claim 1 additionally containing cosmetic adjuvants selected from the group consisting of thickeners, softeners, humectants, surfactants, preserving agents, antifoams, perfumes, oils, waxes, lanolin, lower monoalcohols and polyols, benzoates of $C_{12}$–$C_{15}$ alcohols, propellants, dyes and pigments.

7. A cosmetic composition according to claim 1 in the form of an oily, alcoholic or oleoalcoholic lotion, an emulsion, an oleoalcoholic, alcoholic or hydroalcoholic gel, a solid stick, a spray or an aerosol.

8. A cosmetic composition according to claim 1 for application to the skin containing 0.25 to 3% by weight of a diorganopolysiloxane of formula (1) or formula (2), or mixtures thereof.

9. A cosmetic composition according to claim 1 for protection against sunlight containing 0.5 to 15% by weight of a diorganopolysiloxane of formula (1) or formula (2), or mixtures thereof.

10. A cosmetic composition according to claim 9 for protection against sunlight additionally containing an agent filtering out the UV-B and/or UV-A rays, the total quantity of sunscreens being between 0.5 and 15% by weight relative to the total weight of the composition.

11. Cosmetic composition according to claim 1 for application to the hair, in the form of a shampoo, lotion, gel or rinsing emulsion, which comprises 0.25 to 5% by weight of a diorganopolysiloxane of formula (1) or (2).

12. A method for protecting the skin or hair against ultraviolet radiation which comprises applying to the skin or hair an effective quantity of a cosmetic composition containing a diorganopolysiloxane having a 3-benzylidenecamphor functional group, said diorganopolysiloxane having either of the formulas:

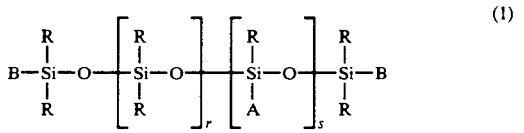 (1)

and

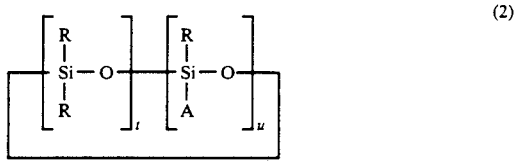 (2)

in which:
substituents R, which can be identical or different, are $C_1$–$C_{10}$ alkyl, phenyl or 3,3,3-trifluoropropyl, at least 80% of substituents R being methyl,
A is a radical of formula:

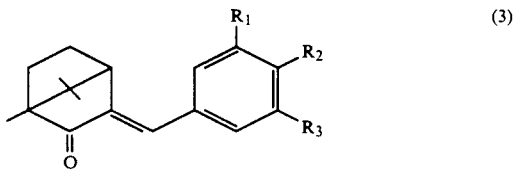 (3)

$R_1$ and $R_2$ independently represent hydrogen, $C_1$–$C_6$ alkyl, $C_1$–$C_6$ alkoxy, hydroxyl, trimethylsilyloxy or a divalent radical Y of formula:

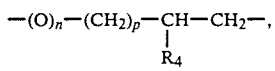

one of $R_1$ and $R_2$ necessarily representing Y,
$R_4$ is hydrogen or $C_1$–$C_4$ alkyl,
n is 0 or 1,
p is an integer from 1 to 10 inclusive,
$R_3$ is hydrogen, $C_1$–$C_6$ alkyl, or $C_1$–$C_6$ alkoxy,
substituents B, which can be identical or different, are R or A,
r is an integer from 0 to 200 inclusive,
s is an integer from 0 to 50 inclusive, provided that if s is 0, at least one of B is A,
t is an integer from 0 to 20 inclusive,
u is an integer from 1 to 20 inclusive, provided that t+u is equal to or greater than 3.

13. A method in accordance with claim 12, wherein said diorganopolysiloxane has at least one of the following characteristics:
R is methyl,
B is methyl,
r is between 5 and 20 inclusive,
s is between 2 and 15 inclusive,
t+u is between 3 and 10 inclusive,
$R_1$ is H or methoxy,
$R_2$ is H or methoxy,
one of $R_1$ and $R_2$ necessarily representing Y wherein n is 0 or 1,
p is 1,
$R_4$ is H or methyl,
$R_3$ is H or methoxy.

14. A method in accordance with claim 12 wherein said cosmetic composition contains a polydimethylsiloxane containing 4'-allyloxy-3-benzylidenecamphor grafts of formula (1), in which R and B are methyl, r is 7 and s is 8.

15. A method in accordance with claim 12 wherein said cosmetic contains a polydimethylsiloxane containing 4'-allyloxy-3'-methoxy-3-benzylidenecamphor grafts of formula (1), in which R and B are methyl, r is 10 and s is 10.

16. A method in accordance with claim 12 wherein said cosmetic contains a polydimethylsiloxane containing 3'-allyl-4'-methoxy-3-benzylidenecamphor grafts of formula (1), in which R and B are methyl, r is 12 and s is 8.

17. Method for protecting a cosmetic composition against ultraviolet rays which comprises incorporating in said composition an effective quantity of at least one diorganopolysiloxane having a 3-benzylidene-camphor functional group, said diorganopolysiloxane having either of the formulas:

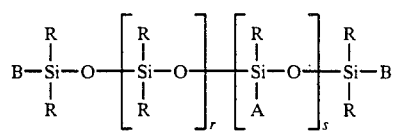

and

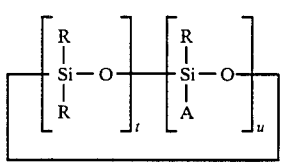

in which:
substituents R, which can be identical or different, are $C_1$–$C_{10}$ alkyl, phenyl or 3,3,3-trifluoropropyl, at least 80% of substituents R being methyl,
A is a radical of formula:

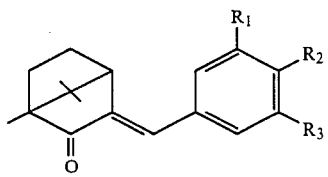

$R_1$ and $R_2$ independently represent hydrogen, $C_1$–$C_6$ alkyl, $C_1$–$C_6$ alkoxy, hydroxyl, trimethylsilyloxy or a divalent radical Y of formula:

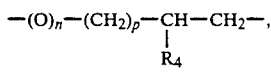

one of $R_1$ and $R_2$ necessarily representing Y,
$R_4$ is hydrogen or $C_1$–$C_4$ alkyl,
n is 0 or 1,
p is an integer from 1 to 10 inclusive,
$R_3$ is hydrogen, $C_1$–$C_6$ alkyl, or $C_1$–$C_6$ alkoxy,
substituents B, which can be identical or different, are R or A,
r is an integer from 0 to 200 inclusive,
s is an integer from 0 to 50 inclusive, provided that if s is 0, at least one of B is A,
t is an integer from 0 to 20 inclusive,
u is an integer from 1 to 20 inclusive, provided that t+u is equal to or greater than 3.

* * * * *